(12) United States Patent
Bachmann

(10) Patent No.: US 7,238,191 B2
(45) Date of Patent: Jul. 3, 2007

(54) SURGICAL RING FEATURING A REVERSIBLE DIAMETER REMOTE CONTROL SYSTEM

(75) Inventor: Michel Andre Bachmann, Vaux sur Morges (CH)

(73) Assignee: Endoart S.A., PSE Ecublens (VD) (CH)

( * ) Notice: Subject to any disclaimer, the term of this patent is extended or adjusted under 35 U.S.C. 154(b) by 256 days.

(21) Appl. No.: 10/653,808

(22) Filed: Sep. 3, 2003

(65) Prior Publication Data
US 2005/0251182 A1 Nov. 10, 2005

(30) Foreign Application Priority Data
Sep. 4, 2002 (EP) ................... 02019937

(51) Int. Cl.
*A61B 17/08* (2006.01)
(52) U.S. Cl. ............... 606/151; 606/139; 606/141; 606/157
(58) Field of Classification Search ........ 606/139–141, 606/153, 37, 30, 31; 24/23 EE, 20 EE, 284, 24/285; 600/29–31, 37; 128/100–111.1, 128/876; 604/909
See application file for complete search history.

(56) References Cited

U.S. PATENT DOCUMENTS

| | | | |
|---|---|---|---|
| 3,840,018 A | 10/1974 | Heifetz | |
| 4,118,805 A | 10/1978 | Reimels | .............. 3/1 |
| 4,881,939 A | 11/1989 | Newman | |
| 5,074,868 A | 12/1991 | Kuzmak | |
| 5,226,429 A | 7/1993 | Kuzmak | |
| 5,449,368 A | 9/1995 | Kuzmak | |
| 5,601,604 A | 2/1997 | Vincent | |
| RE36,176 E | 3/1999 | Kuzmak | |
| 5,938,669 A | 8/1999 | Klaiber et al. | |
| 6,074,341 A * | 6/2000 | Anderson et al. | .............. 600/29 |
| 6,102,922 A | 8/2000 | Jakobsson et al. | |
| 6,511,490 B2 | 1/2003 | Robert | |
| 6,547,801 B1 * | 4/2003 | Dargent et al. | .............. 606/157 |
| 2003/0073880 A1 | 4/2003 | Polsky et al. | |

FOREIGN PATENT DOCUMENTS

FR WO 01/10359 A1 * 2/2001

(Continued)

*Primary Examiner*—Glenn K. Dawson
*Assistant Examiner*—Michael G. Mendoza
(74) *Attorney, Agent, or Firm*—Nicola A. Pisano, Esq.; Luce, Forward, Hamilton & Scripps LLP

(57) ABSTRACT

A surgical ring, designed to be implanted around biological organs comprising a pouch or a duct, so as, on the one hand, to form a closed loop between these two extremities (1, 2), thus forming a first (1) and a second (2) extremity and, on the other hand, to reduce the diameter of the opening of the organ when it is tightened by the ring, the ring including a system for reversibly controlling the variation in its diameter. The system also includes a flexible filiform element (4), inserted longitudinally with possibility of sliding into the material constituting the body of the ring between the first (1) and second (2) extremities, so as to define a fixed portion (5) connected to the first extremity (1) and a free portion (7) associated with an actuator (8) mounted on the ring near the second extremity (2).

33 Claims, 3 Drawing Sheets

FOREIGN PATENT DOCUMENTS

| | | |
|---|---|---|
| FR | 2855744 A1 * | 12/2004 |
| WO | WO 00/15158 | 9/1999 |
| WO | WO 01/49245 A2 | 2/2001 |
| WO | WO 01/49245 A3 | 2/2001 |
| WO | WO2003105732 | 12/2003 |
| WO | WO2004019671 | 3/2004 |

* cited by examiner

SURGICAL RING FEATURING A REVERSIBLE DIAMETER REMOTE CONTROL SYSTEM

CROSS REFERENCE TO RELATED APPLICATIONS

This application claims priority to European Patent Application No. EP-02 019937.8, filed Sep. 4, 2002.

FIELD OF THE INVENTION

The present invention relates to the technical field of surgical implants designed to be implanted in the body of a patient, around biological organs having a pouch or duct, and, more specifically, to gastric rings concepted to treat obesity by implantation of a flexible gastric ring. This ring is designed to form a closed loop around the stomach, in order to reduce the diameter of the opening of the stoma. The invention relates more specifically to the remote-control gastroplasty rings, involving no invasive operation whatsoever after its installation.

The present invention involves a surgical ring designed to be implanted in the body of a patient around biological organs comprising a pouch or a duct. On the one hand this forms a closed loop between its two extremities. This forms, respectively, a first and second extremity and, on the other hand, reduces the diameter of the opening of said organ when it is constricted by the ring, said ring comprising a system for precise and reversible control of the variation of the diameter of the ring. The control system comprises a flexible filiform element.

The invention involves, more specifically, a gastroplasty ring, but it can also involve a ring designed to be used to treat urinary or fecal incontinence (artificial sphincter), or even a ring conceived to regulate blood flow in blood vessels for example; this list is by no means exhaustive.

More specifically, the present invention involves a remote-control gastroplasty ring that avoids all invasive surgical re-intervention for adjusting the ring's diameter. This ring is then integrated into a system of restriction and remote control of the ingestion of food into the stomach of a patient. It consists of a gastric ring fitted with an actuator connected to a receiving antenna for receiving a control signal, as well as an emitting antenna that is arranged outside the patient to send a control signal to the receiving antenna, then to the actuator.

In its preferred application, the ring in compliance with the invention is controlled by radio frequency. The actuator is, on the one hand, linked to the receiving antenna by a receiving circuit, in which said antenna is installed and, on the other hand, comprises an electric control case linked to an emitting antenna.

BACKGROUND OF THE INVENTION

Surgical intervention is already practiced on patients afflicted with extremely severe obesity (morbid obesity), i.e. in the case of the patient whose weight exceeds, for example the ideal weight of at least 50 kg, by implanting gastroplasty rings in such patients. Such interventions allow not only a series of serious health problems, arising from such overweight, to be avoided, but also and especially to avoid a certain, early death of such patients.

In fact, it is a given fact that patients suffering from morbid obesity see their life expectancy significantly reduced, by at least ten to fifteen years, all the while creating significant psychological burdens. Moreover, a whole series of additional health phenomena are implicated. Their incidence has been implicated in the appearance of additional illnesses such as cardio-vascular illnesses, or even those such as hypertension, diabetes or even severe arthritis.

It is also a given fact that, for such patients, treatments based on strict diets combined with a series of physical exercises, also associated with behavior modification, specifically nutritional, are poorly adapted, even if these treatment methods are acknowledged to be the safest.

This is the reason why effective, long-term treatments for morbid obesity call for surgical intervention.

In general, surgical treatment techniques are recognized that make use of a flaw in the absorption of foodstuffs, i.e. a shortening of the food passage and of digestive successes and techniques making use of a gastric restriction that reduces the size of the stomach.

Surgical techniques implicating a flaw in absorption are those implicating, for example, a "by-pass" technique, or small intestine bypass, or even those implementing a separation of the alimentary passage relative to the digestive successes. These surgical techniques are relatively major and may give rise to severe complications, and this is the reason for which they are almost never used any more now.

Now the tendency is to use surgical techniques which make use of less drastic surgical interventions, such as gastric restriction involving the installation of a gastric ring.

These techniques are now in fairly common use, and for the most part they use, as described for example in patent U.S. Pat. No. 5,074,868, a flexible band of elastomeric material designed to be implanted around the stomach, forming a closed loop defining a fixed pre-established ring diameter, thanks to a closure system. The body of the flexible band comprises a compression cavity or chamber, of variable volume, which is linked to an adjustment catheter allowing injection or extraction of fluid in the compression chamber, so as to cause the internal diameter of the loop to vary, in order to change or adjust the diameter of the stoma. In this way, in combination with the pre-established and fixed ring diameter, which allows adjustment of the stoma diameter and therefore regulation of the quantity of food ingested.

These known devices generally offer satisfaction, but nevertheless have a certain number of drawbacks linked essentially to difficulties stemming from the surgical interventions carried out after installation of the gastric ring. In effect, it has been shown that, in spite of the possibility of being able to modify, to a certain extent, the diameter of the ring without major surgical intervention, thanks to the presence of a miniature case implanted under the skin of the patient, installation of such rings may be accompanied by intolerance phenomena, accompanied for example by vomiting. This may be linked to various causes, and notably to too great a reduction in the diameter of the stoma, or even to an ineffective action of the ring, associated with too great a stoma diameter, or even merely an obstruction, infection or local or general inflammation.

This is the reason why it is often shown to be necessary to once again perform surgical intervention, either to relieve the patient, or to adjust or change the ring implanted previously. Such surgical intervention is particularly severe and most often requires cutting of the ring by a surgeon, along with its changing and replacing.

Finally, such operations are difficult to carry out, difficult for the patient to tolerate, and costly, all the more because they involve destruction and replacement of a ring.

Along with these classic techniques, we also establish a progressive and gradual loss of pressure inside the ring, due to natural osmotic phenomena across the device wall. This necessitates regular interventions in order to readjust the diameter of the ring and contributes to the increased need for the constant surveillance of the patient.

Finally, it has been established that it is possible to use a simple syringe, generally filled with physiological water, to ensure diametric readjustment of the ring by injecting liquid through a subcutaneous case attached to the ring. This is an operation which, because of its simplicity, can escape all medical inspection and be carried out by the patient himself. Optimal safety and control conditions are not, therefore, fulfilled in the case of classical techniques.

To attempt to resolve these drawbacks, a solution has already been proposed, such as that described in the patent application EP-0 876 808. This is a gastric ring that is adjustable in a non-invasive manner, with no patient discomfort, done by remote control, without invasive surgical intervention, by an electromagnetic means implanted in the body of the patient and mounted at least in part on the gastric ring. The means implemented comprise a control box, implanted in the ring and attached to a fluid reservoir, which is also implanted in the body of the patient. With the help of a pump controlled from outside the patient's body through electromagnetic means, it injects or withdraws fluid in the gastric ring in order to adjust its diameter. The entire device is under the control of a means of external control, of the micro-computer type, equipped with an emitter-receiver radio, for example, under the control of the practicing physician.

Such a device, of course, indicates an interesting and beneficial development for patients, but which nevertheless suffers from a certain number of drawbacks linked, in particular, to the need to implant the fluid reservoir directly into the body of the patient. This implantation is delicate and it is difficult to make it watertight, which could present a danger to the patient. Moreover, such a device requires a source of internal energy, for example a battery, implanted in the body itself of the patient, which once again complicates surgical intervention and especially confers a certain fragility upon the system, and could necessitate surgical intervention to change the battery.

OBJECTS AND SUMMARY OF THE INVENTION

Consequently, the invention seeks to remedy the various drawbacks listed above, and to propose a new surgical ring that has a reversible diameter control system. This system is particularly simple, reliable and effective, notably with regard to precision and efficiency, such that it can be integrated into a remote control system that does not require significant control energy.

Another object of the invention seeks to propose a new surgical ring, notably gastric, whose mechanical control is particularly precise.

Another object of the invention seeks to propose a new surgical ring, notably gastric, which is of a circular shape during use, all the while offering great control safety.

Another object of the invention seeks to propose a new surgical ring, notably gastric, which allows implementation of mechanical means that are particularly well tested and resistant, so as to obtain a gastric ring of great sturdiness and good longevity.

Another object of the invention seeks to propose a new surgical ring, notably gastric, which, while allowing good control of the variation of the diameter of the ring, is likely to minimize intolerance phenomena in the patient.

Another object of the invention seeks to propose a new surgical ring, notably gastric, whose control system is particularly thrifty with regard to energy usage.

Another object of the invention seeks to propose a new gastric ring of greatly reduced bulk, which allows easy implantation in the patient's stomach.

Another object of the invention seeks to propose a new surgical ring, notably gastric, which allows good division of all closure forces of the ring on the stomach.

Another object of the invention seeks to propose a new system of restriction and remote control of ingestion of food into the stomach of a patient that is particularly effective, very sturdy and long-lived, while at the same time requiring relatively low supply energy.

The objects assigned to the invention are achieved with the help of a surgical ring, designed to be implanted in the body of a patient around biological organs having a pouch or a duct so as, on the one hand, to form a closed loop between its two extremities, thus forming a first and second extremities and, on the other hand, reduce the diameter of the opening of the biological organ when it is tightened by the ring, said ring comprising a system to reversibly control the variation in its diameter, said system comprising a flexible filiform element, characterized in that:

said flexible filiform element is inserted longitudinally with possibility of sliding into the material forming the body of the ring, substantially between the first and second extremities, in order to define a fixed portion united with the first extremity and a free portion, functionally associated with an actuator mounted on the ring, near the second extremity, such that the actuator may ensure reversible translation of the flexible filiform element in order to obtain a variation associated with the diameter of the ring, said free portion features a means of force cooperation with the actuator, said means of force cooperation being formed of a screw thread pitch.

The objects assigned to the invention are also achieved with the help of a system of restriction and remote control of the ingestion of food into the stomach of a patient, comprising:

A gastric ring, as defined previously and comprising, as an actuator, an electric motor that is linked to a receiving antenna in order to receive a control and power signal.

An emitting antenna arranged outside the patient, in order to send a control and power signal to the receiving antenna, said emitting antenna being functionally linked to a control interface.

BRIEF DESCRIPTION OF THE DRAWING

Other objects and advantages of the invention will become more apparent upon reading the attached description, as well as with the help of the attached drawings, which are given strictly for illustration and information purposes, in which.

MORE DETAILED DESCRIPTION

In the following description, reference will be made, solely as an example, to a gastric ring concepted for implantation around the stomach in order to reduce the diameter of opening of the stoma, or around the esophagus. In effect, the invention is in no way limited to this application, and on the contrary seeks to cover other surgical rings, such as those used to treat urinary or fecal incontinence, or those used around blood vessels in order to regulate blood flow.

In the case of treatment of urinary continence, the ring will be implanted around the bladder or urinary tracts, and in the case of fecal incontinence, it will be implanted around gastrointestinal tracts, and notably around anal structures of the intestine.

FIGS. 1 to 10 illustrate a gastric ring in compliance with the invention, designed to be implanted around the stomach of a patient, by forming a substantially circular loop, in order to cause gastric restriction by reducing the diameter of the opening of the stomach. The gastric ring in compliance with the invention is shown in the form of a flexible tubular band, whose flexible and elastic envelope has a smooth surface, making it atraumatic so that it is easily tolerated by the patient and the tissues of the stomach. The band is made, for example, from elastomeric material.

Figure 5:
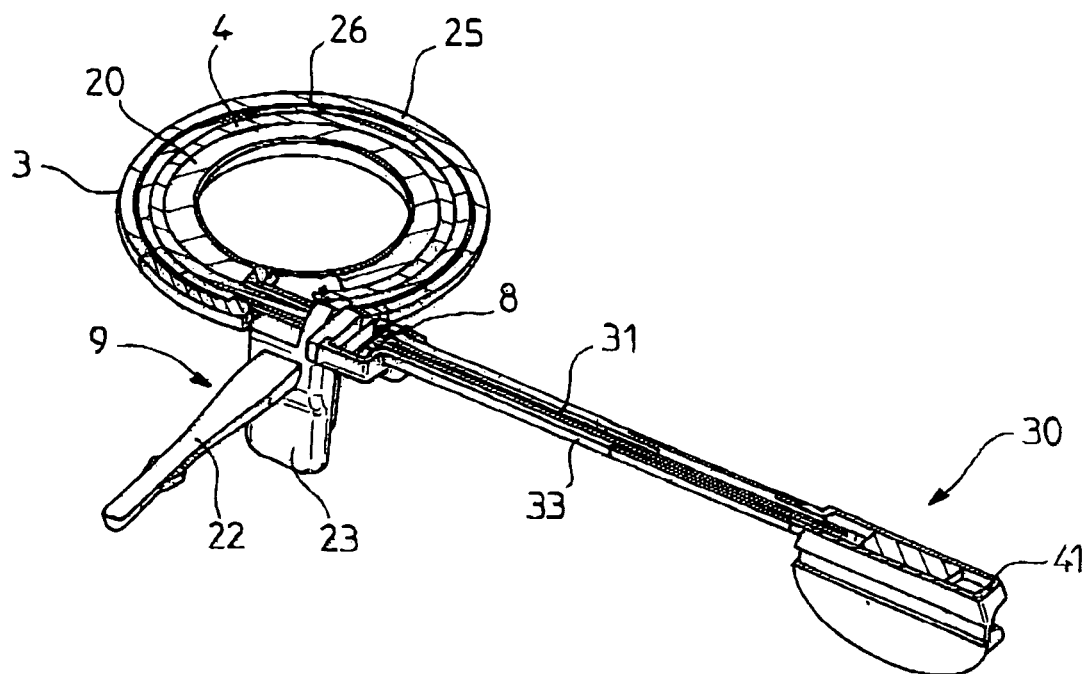
FIG. 5 shows, according to a perspective view and a partial longitudinal section view, an example of embodiment of a gastric ring in compliance with the invention and corresponding to the second variation of embodiment illustrated in FIG. 3, said ring being equipped with a receiving antenna in the extended position.
Figure 6:
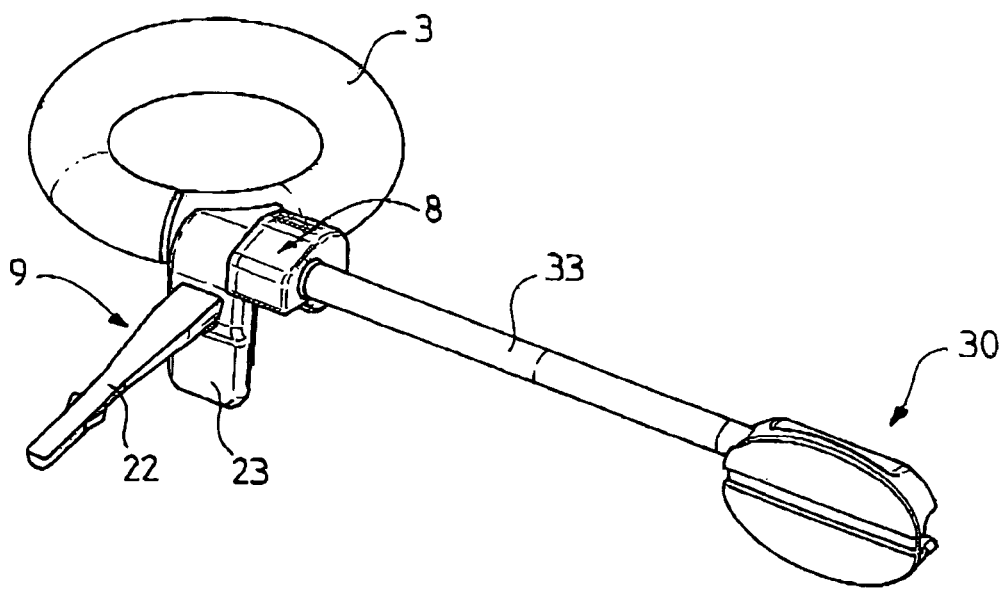
FIG. 6 shows, according to a perspective view, a gastric ring identical to that illustrated in FIG. 5, the receiving antenna being in the extended, functioning position.

The flexible tubular band comprises two extremities, respectively 1 and 2, on which means of closure 9 are shaped and implanted (FIGS. 5 and 6). The last are intended to cooperate in such a way as to ensure latching and closure of the ring around the stomach, in order to create a closed loop between the two extremities 1 and 2, thus forming, respectively, a first and a second extremity.

The gastric ring in compliance with the invention is shown in the shape of a torus of revolution, of cross-section, for example, that is substantially cylindrical, delimited on the outside by a mono-layer or multi-layer envelope 3. This envelope could advantageously be made of a protective covering, for example, based on or made of silicone.

Figure 1:
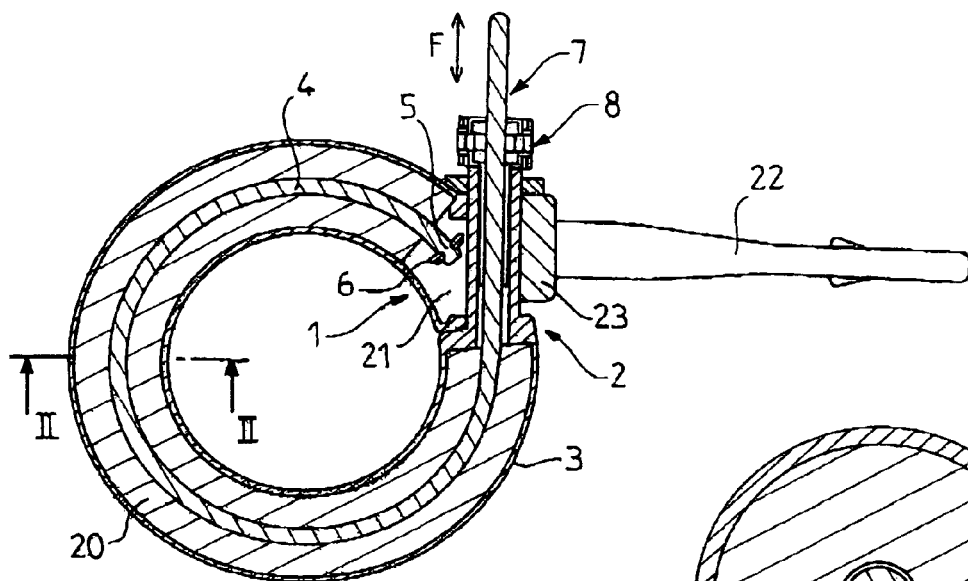
FIG. 1 shows, according to a longitudinal section view, an example of a first variation of embodiment of a gastric ring in compliance with the invention.
Figure 3:
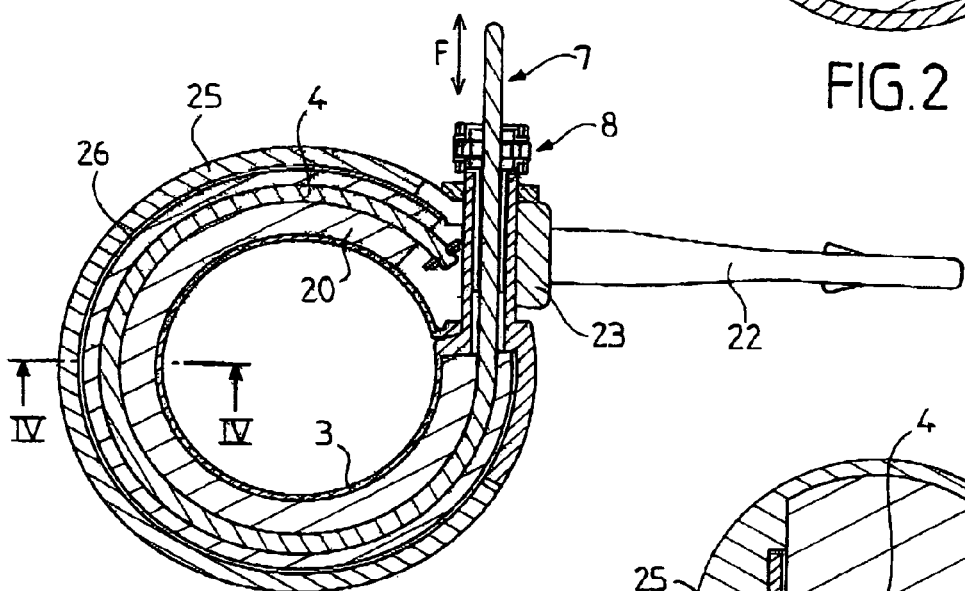
FIG. 3 shows, according to a longitudinal section view, a second variation of embodiment of a gastric ring in compliance with the invention.

As shown in particular in FIGS. 1 and 3, the gastric ring in compliance with the invention consists, advantageously, of a flexible filiform element 4 having good flexibility and a good mechanical resistance. It is inserted longitudinally, with possibility of sliding along the principal axis of symmetry of the cylinder, or of the main body of the ring. Said element 4 occupies the cavity linking the first and second extremities 1 and 2 and extends substantially between the first and second extremities 1 and 2, i.e. substantially all along the developed length of the ring.

As shown in the figures, the flexible filiform element 4 is mounted so as to define a fixed portion 4 which is consolidated with the help of a means of consolidation 6, which, for example, makes use of a retaining ring and a washer, or any equivalent means, with the first extremity 1 of the ring. The other terminal portion of the flexible filiform element 4 which forms a free portion 7, i.e. that which might shift by translation relative to the fixed portion 5. Said free portion 7 is functionally associated with an actuator 8 mounted on the ring, near or on the level of the second extremity 2. Actuator 8 is used to transmit the energy necessary to ensure, when it is activated, the reversible translation of the flexible filiform element 4 to the interior of the ring, i.e. the reversible shift of free portion 7 relative to fixed portion 5, with a view to obtaining an associated change in the ring's perimeter, i.e. an increase or reduction in its diameter.

Direct mounting of the actuator 8 on one of extremities 2 of the ring also allows a significant gain in space and a good mechanical efficiency.

Advantageously, the free portion 7, extending, for example, along a length on the order of a few centimeters, or along the entire length of the flexible filiform element, is provided with a means of force cooperation 10 (FIG. 10) with actuator 8. This means 10 is designed to ensure transmission of energy supplied by actuator 8 to the entire flexible filiform element 4, starting from its support point, consisting of the fixed portion 5.

Figure 10:
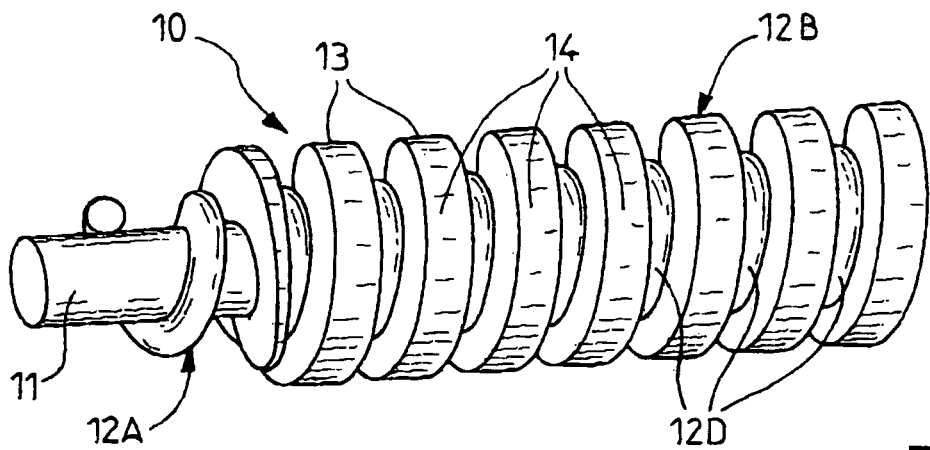
FIG. 10 shows, according to a partial perspective view, an embodiment detail of the flexible filiform element in compliance with the invention, and whose function is to adjust the ring diameter.

Advantageously, and as shown in FIG. 10, the means of force cooperation 10, consist of a screw thread pitch.

According to the invention, the flexible filiform element 4 has sufficient flexibility so that it can be adapted to the substantially circular shape of the ring, while at the same time being able to transmit the force necessary for adjustment of the ring diameter. Advantageously, the flexible filiform element 4 consists of a flexible core 11, preferably metal, for example of circular cross section, on which is fixed, and wound coaxially, for example over its whole length, at least one un-joined coil spring which comprises the screw thread pitch.

In a particularly ideal way, flexible filiform element 4 comprises two un-joined coil springs which form the screw thread pitch, respectively, a first spring 12A, wound helicoidally along the flexible core 11, and a second spring 12B of greater exterior diameter, such as that shown in FIG. 10, and preferably comprising coils 14 of rectangular transverse section 13, so as to delineate a flat external generatrix. Said first spring 12A is interposed between coils 14 of the second spring 12B in order to maintain a constant square screw thread pitch.

Thanks to this arrangement, it is possible to keep constantly a thread pitch that is substantially constant and effective, even in the case of deformation of the flexible filiform element 4. This confers a great precision and effectiveness on the device, while at the same time being low in energy costs required for its function by reason of the high efficiency of the transmission by a square screw thread pitch.

Thanks to this arrangement, it is possible to guarantee a stable adjustment position even when no energy is provided to the system.

The second spring 12B may be advantageously obtained by laser cutting of a cylindrical hollow tube. Its sturdy mounting between loops 12D of the first spring 12A is done using longitudinal traction. The second spring 12B is therefore naturally activated with an intrinsic elastic compression force which tends to make the loops jointed. This intrinsic force is thrown down by loops 12D of the first spring 12A, against which they are supported. We also have the benefit of a constant feed despite the natural and indispensable elasticity and flexibility of the flexible elongated element 4.

Actuator 8 may be of any classical means known to the craftsman which could fit with the screw thread pitch so as to transmit movement to it. In a particularly ideal way, actuator 8 may be provided with a simple bolt which allows assurance of screw thread pitch drive. Actuator 8 may, in general, be by means of a motor, an electric or electromagnetic motor, or otherwise, without however deviating from the scope of the invention.

As a variation of realisation not shown in the illustrations, it is of course possible to replace the screw thread pitch described above by any equivalent technical means and, for example, by a mesh rack on actuator 8, featuring a gear or an equivalent means. We can also envision making the flexible filiform element 4 in the shape of a simple cable, driven reversibly by an actuator 8 integrating a pulley.

As shown in the figures, the gastric ring in compliance with the invention, generally speaking, whose body consists mainly of a compressible material 20 and which fills the interior of envelope 3. Flexible filiform element 4 is inserted longitudinally and substantially into the compressible material 20, with the possibility of sliding, as shown in the example in FIGS. 2 and 4.

In a particularly ideal manner, compressible material 20 is ePTFE, whose compressibility and stability characteristics in constriction are particularly well suited to this type of application.

Figure 2:
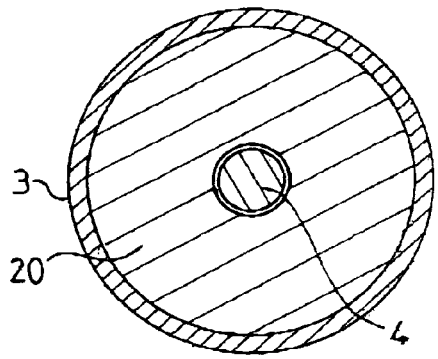
FIG. 2 shows a transverse section view of the gastric ring shown in FIG. 1, said cutaway being made according to line II—II of FIG. 1.

According to a first variation of embodiment, as shown in FIGS. 1 and 2, the ring in compliance with the invention consists of an envelope 3 made of silicone material and of a thickness that is substantially constant, which comprises the watertight exterior covering of the ring. The interior covering of the ring is made exclusively of compressible material 20, for example ePTFE, inside of which the flexible filiform element 4 is inserted with a slight clearance.

Extremity 1 comprises a pouch 21, which for example is filled with glue, and in which is mounted and fixed, the fixed portion 5, with means of consolidation 6.

As shown in FIGS. 1 and 2, extremity 1 is provided with a tab 22 which extends towards the exterior of the ring, and is designed to fit with a complementary female element 23, which is integral to the same extremity 1 of the ring. The ring constitutes closure means 9, which leads to latching of the ring and forms, for example, a loop around extremity 2.

According to this first variation of production, the action of the actuator 8 on the flexible filiform element 4 transmits an actuating force according to one of the directions indicated by arrow F illustrated in FIG. 1. The consequence of this is to compress or release, in a substantially longitudinal way, compressible material 20 which translates by a variation associated with the ring's diameter, both internal and external, substantially in the manner of a slip knot.

Figure 4:
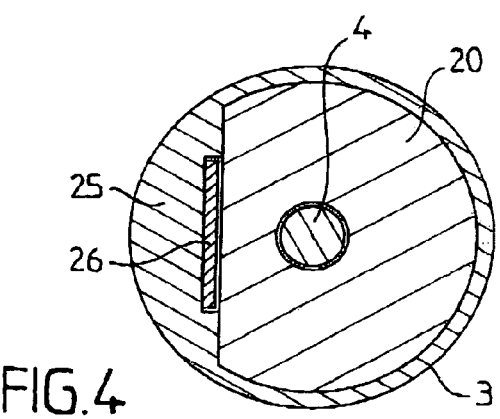
FIG. 4 shows the transverse cross section of the gastric ring illustrated in FIG. 3, said section being made along line IV—IV of FIG. 3.

The second variation of embodiment illustrated in FIGS. 3 and 4 differs from the one illustrated in FIGS. 1 and 2 only in the specific arrangement of the external envelope 3, whose dorsal periphery 25 is reinforced with a view to clipping the external radial extension or centrifugal of the ring. This, on the contrary, favors internal radial or centripetal variation of the diameter of the ring. In this way, we favor radial variation of the ring diameter at its internal periphery, which is opposite its dorsal periphery.

As shown, the dorsal periphery 25 may be made in the form of an external envelope 3 of which only the dorsal periphery has an allowance, i.e. an external dorsal thickness that is greater than the rest of the external envelope (FIG. 4). Alternatively, or complementarily, dorsal periphery 25 may also be made using a polymeric material of greater hardness than the hardness of the rest of the polymer material envelope 3. It is also conceivable, as shown in FIG. 4, to provide for integrating, in the reinforced dorsal periphery 25, a reinforcing insert 26, preferably metallic, extending over the majority of the ring's periphery between compressible material 20 and dorsal periphery 25. Advantageously, insert 26 can have a shape memory that is substantially circular, in order to attain an elastic circular rest position of the ring.

Thanks to this arrangement, increase or reduction of the ring's diameter is limited to a reversible radian displacement, located at the level of the internal periphery of the ring opposite the dorsal periphery, which translates into a variation of the ring's internal diameter in the centrifugal or centripetal direction, according to the direction of the stress imparted to the flexible filiform element 4, indicated by one of the directions of arrow F.

The gastric ring in compliance with the invention is particularly concepted to be integrated into a system of restriction and remote control of food ingestion in the stomach of a patient, in such a way as to be able to remotely control the variation of the ring's diameter without any invasive surgical intervention. To this end, actuator 8 is an electric motor which, advantageously, is linked to a subcutaneous receiving circuit provided with a receiving antenna 30 (FIGS. 5 to 7) for reception of a radio frequency control and power signal, all of which is designed to be implanted in the patient's body.

Figure 7:
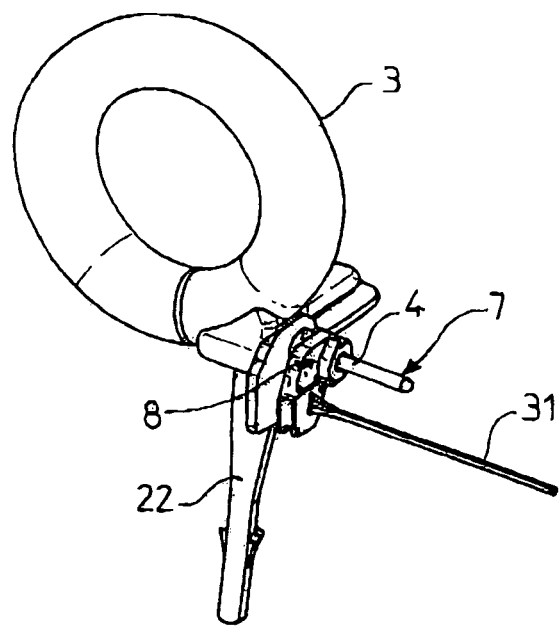
FIG. 7 illustrates, according to a perspective view, a gastric ring in compliance with the invention, illustrating the extended electrical connection wires.

As illustrated notably in FIGS. 5 to 7, the electric motor is consolidated with extremity 2, so that it can be located outside the ring, since the electric motor is provided, in the standard manner, with a set of bearings and gears, which are functionally linked with an electrical connection 31 to the receiving circuit antenna 30.

In this preferred application, the electric motor has no internal sources of supply at all, because its energy is provided by the receiving circuit 30. This converts radio frequency waves received from the control unit through the exterior antenna, into a motor control signal and energy, ensuring its electrical supply. Receiving antenna 30 is adapted and chose to receive a control signal and a power signal at the same time.

The low energy requirement of the electric motor allows control orders and activating energy to be sent by radio frequency to the motor, avoiding any need to have to implant an additional source of energy, such as a battery or battery cell, in the body of the patient.

As shown in FIG. 5, the electric motor is linked to the receiving antenna 30 by electrical connection 31, which is protected by a protection duct 33. This ensures watertightness. At its extremity is mounted said receiving circuit, which comprises receiving antenna 30. The free portion 7 of the flexible filiform element is also integral to duct 33 in such a way as to achieve a perfectly protected assembly, watertight and which will irritate the surrounding tissues as little as possible.

In a particularly ideal way, said receiving antenna circuit is elastically collapsible (FIGS. 8 and 9), so that the surgeon may momentarily reduce the dimensions of the implantable part of the system, i.e. the ring, duct 33 and receiving antenna circuit 30. This enables the monoblock assembly to pass through a small-dimension trocar, preferably of a diameter less than, for example, 15 mm, in order to facilitate implantation.

Figure 8:
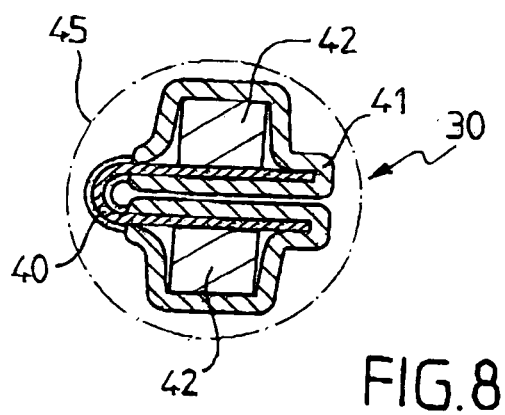
FIG. 8 shows, according to a transverse section view, the collapsed position of the ring's receiving circuit with the receiving antenna.
Figure 9:
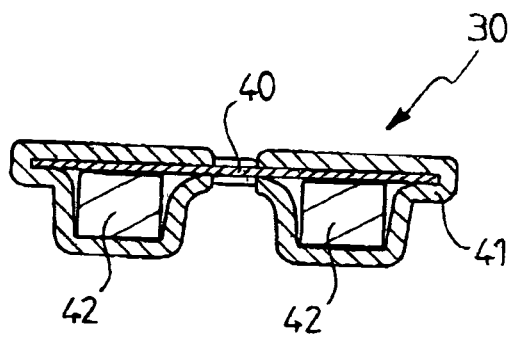
FIG. 9 shows, according to a transverse section view, the receiving circuit with its antenna in the extended position.

As shown in FIGS. 8 and 9, the collapsible receiving antenna circuit 30 shall be advantageously but not necessarily flexible, either entirely, or at least in part, and shall consist of a flexible electronic circuit 40, shown for example in the shape of a disk covered with a silicone envelope 41. This latter also serves as protection for electronic components 42, connected and functionally linked to the antenna itself of flexible circuit 40.

According to a particularly ideal version of the invention, the receiving antenna circuit 30 shall be shown in the shape of a piece, for example, in the shape of a disk that is collapsible onto itself, substantially according to the diameter of the disk as shown in FIGS. 5 and 6.

Thanks to this arrangement and to the elasticity and flexibility properties of the selected materials, it is also possible, starting from the extended position of antenna circuit 30, as shown in FIGS. 6 and 9, to collapse the antenna circuit 30 along its diameter. This way it occupies a restricted volume (FIG. 8), which allows its insertion into a circular trocar, whose shape 45 is shown in the dotted line in FIG. 8.

The system of restriction and remote control in compliance with the invention also consists of an emitting antenna (not shown in the illustrations), arranged outside the patient to send a control and power signal to receiving antenna 30. Said emitting antenna is itself linked to the function of a control interface, such as a PC or any other equivalent means at the disposal of the treating physician During its use and, once the gastric ring in compliance with the invention has been implanted, with its receiving circuit, featuring antenna 30 in the extended position, in the patient's body, the practicing physician may position the emitting antenna in the face-to-face position with the receiving antenna 30 on the skin of the patient. The doctor may then send a control and power signal in the direction of the receiving antenna 30, to transmit to it, at the same time, energy required to activate actuator 8 and, at the same time, control the direction of its shift.

Thanks to the system of restriction and remote control in compliance with the invention, it is thus possible to vary the diameter of the gastric ring without having to undertake invasive surgical intervention, and this variation may be carried out at will, because multiple control cycles may be carried out at regular or irregular intervals, solely under the control of the treating physician.

The system has been shown to be particularly reliable, because only the treating physician has the control box, comprising the emitting antenna, which allows him to exert total control over the diameter adjustment. The patient cannot, therefore, have free access to any means of adjusting the diameter of the ring.

Therefore, the invention involves a new surgical and therapeutic treatment procedure, implementing a system of restriction and remote control of food ingestion according to the invention.

What is claimed is:

1. Apparatus for regulating the functioning of a patient's organ or duct, comprising:
   an elongated member having first end and second ends, the elongated member having a substantially smooth, atraumatic ventral surface;
   a clip disposed on the first end of the elongated member, the clip configured to engage the second end of the elongated member so that the elongated member forms a loop around the organ or duct;
   a flexible element slidably disposed within the elongated member, the flexible element defining a helical screw thread; and
   a telemetrically-controlled actuator disposed on the second end of the elongated member, the actuator having a nut that engages the helical screw thread, operation of the actuator causing the nut to draw the helical screw thread therethrough, whereby the flexible element constricts the loop against the patient's body organ or duct.

2. The apparatus of claim 1 wherein the elongated member comprises a protective covering.

3. The apparatus of claim 1 wherein the apparatus is configured for laparoscopic introduction.

4. The apparatus of, claim 3 wherein the clip further comprises a tab extending from the first end of the elongated member, the tab configured to pass through and engage an aperture disposed in the second end of the elongated member.

5. The apparatus of claim 1 wherein a portion of the flexible element comprises a spring.

6. The apparatus of claim 5 wherein the helical screw thread comprises:
   a core wire;
   a first helical spring disposed on the core wire, the helical spring having a square transverse profile; and
   a second helical spring interwound with the first helical spring to define a pitch of the first helical spring and to permit flexion of the helical screw thread, while maintaining the pitch substantially constant.

7. The apparatus of claim 1 wherein the elongated member comprises an elongated tube of compressible material that renders the ventral surface of the elongated member compressible.

8. The apparatus of claim 7 wherein the compressible material is ePTFE.

9. The apparatus of claim 1 wherein the telemetrically-controlled actuator further comprises:
   an electric motor coupled to the nut;
   an antenna; and
   an electronic circuit electrically coupled to the antenna and the electric motor.

10. The apparatus of claim 9 wherein the antenna and electronic circuit are disposed within an elastomeric envelope.

11. The apparatus of claim 10 wherein the elastomeric envelope has a substantially flat profile after subcutaneous deployment.

12. The apparatus of claim 11 wherein the electronic circuitry and the antenna are collapsible.

13. The apparatus of claim 2 wherein the dorsal periphery of the elongated member is reinforced to prevent diametral expansion of the dorsal periphery.

14. The apparatus of claim 13 wherein a dorsal thickness of the protective envelope is greater than a ventral thickness of the protective envelope.

15. The apparatus of claim 13 wherein a dorsal hardness of the protective envelope is greater than a ventral hardness of the protective envelope.

16. The apparatus of claim 13 further comprising a reinforcing insert.

17. The apparatus of claim 1 wherein the elongated member comprises a gastric ring designed to be implanted around a patient's stomach or esophagus.

18. The apparatus of claim 1 wherein the elongated member comprises a ring designed to be implanted around the bladder or urinary tracts, or around gastro-intestinal tracts or around blood vessels.

19. Apparatus for gastric banding of a patient's stomach, comprising:
an elongated member having first end and second ends, the elongated member having a compressible ventral surface and a substantially rigid dorsal periphery and configured to be formed into a loop around a portion of a patient's stomach;
an electric motor disposed on the second end of the elongated member;
a nut actuator coupled to the electric motor;
a flexible element slidably disposed within the elongated member, the flexible element defining a helical screw thread, the flexible element having a fixed end coupled to the first end of the elongated member and a free end that engages and extends through the nut actuator,
wherein operation of the nut actuator draws the helical screw thread through the nut actuator and causes the flexible element to vary a diameter of the loop.

20. The apparatus of claim 19 wherein a portion of the flexible element further comprises a spring.

21. The apparatus of claim 20 wherein the helical screw thread comprises:
a core wire;
a first helical spring disposed on the core wire, the helical spring having rectangular transverse profile; and
a second helical spring interwound with the first helical spring to define a pitch of the first helical spring, the second helical spring having first and second ends operatively coupled to the core wire end to maintain the pitch substantially constant.

22. The apparatus of claim 19 where the elongated member is reinforced on the dorsal periphery to prevent diametral expansion of the dorsal periphery of the elongated member.

23. The apparatus of claim 22 wherein the elongated member comprises a reinforcing insert.

24. The apparatus of claim 19 wherein the elongated member comprises an elongated tube of compressible material that renders the ventral surface of the elongated member compressible.

25. The apparatus of claim 19 wherein the elongated member further comprises a protective covering.

26. The apparatus of claim 25 wherein the protective covering provides a smooth, atraumatic surface for contacting the patient's stomach.

27. The apparatus of claim 19 further comprising:
an antenna; and
an electronic circuit electrically coupled to the antenna and the electric motor.

28. The apparatus of claim 27 wherein the antenna and electronic circuit are disposed within an elastomeric envelope.

29. The apparatus of claim 28 wherein the elastomeric envelope has a substantially flat profile after subcutaneous deployment.

30. The apparatus of claim 29 wherein the electronic circuitry and the antenna are collapsible.

31. The apparatus of claim 19 wherein the apparatus is configured for laparoscopic introduction.

32. The apparatus of claim 19 further comprising a clip disposed on the first end of the elongated member, the clip configured to engage the second end of the elongated member.

33. The apparatus of claim 32 wherein the clip further comprises a tab extending from the first end of the elongated member, the tab configured to pass through and engage an aperture disposed in the second end of the elongated member.

* * * * *